(12) United States Patent
Shibuya et al.

(10) Patent No.: US 7,560,547 B2
(45) Date of Patent: Jul. 14, 2009

(54) HYDROXYALKYL CYCLIC DIAMINE COMPOUNDS

(75) Inventors: Kimiyuki Shibuya, Tokorozawa (JP); Tadaaki Ohgiya, Tokorozawa (JP); Toru Miura, Higashimurayama (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

(21) Appl. No.: 11/612,137

(22) Filed: Dec. 18, 2006

(65) Prior Publication Data

US 2007/0088159 A1    Apr. 19, 2007

Related U.S. Application Data

(62) Division of application No. 10/733,243, filed on Dec. 12, 2003, now Pat. No. 7,176,306.

(30) Foreign Application Priority Data

Dec. 12, 2002    (JP)    ............... 2002-360899

(51) Int. Cl.
*C07D 243/08*    (2006.01)
*C07D 401/12*    (2006.01)
(52) U.S. Cl. ..................... 540/575; 544/360
(58) Field of Classification Search ............ None
See application file for complete search history.

(56) References Cited

U.S. PATENT DOCUMENTS 4,939,262 A * 7/1990 Bonse et al. ............ 546/311

FOREIGN PATENT DOCUMENTS

WO    WO 98/54153    12/1998

* cited by examiner

*Primary Examiner*—Kamal A Saeed
(74) *Attorney, Agent, or Firm*—Oblon, Spivak, McClelland, Maier & Neustadt, P.C.

(57) ABSTRACT

The present invention is directed to a process for producing a compound (5) from the compound (1).

By use of the compound (1), a variety of cyclic diamine derivatives (5) or salts thereof, useful as drugs, can be produced in an industrially advantageous manner with a constant yield.

1 Claim, No Drawings

HYDROXYALKYL CYCLIC DIAMINE COMPOUNDS

CROSS-REFERENCE TO RELATED APPLICATIONS

This application is a divisional application of prior application Ser. No. 10/733,243 filed Dec. 12, 2003, now allowed.

TECHNICAL FIELD

The present invention relates to a process for preparing hydroxyalkyl cyclic diamine compounds, and to a process for preparing cyclic diamine derivatives and salts thereof.

BACKGROUND ART

Acyl coenzyme A cholesterol acyltransferase (ACAT) is an enzyme serving for catalyzing the synthesis of cholesteryl ester from cholesterol, playing an important role in the metabolism of cholesterol and intake of cholesterol in the digestive organs.

In recent years, it has been clarified that when the activity of ACAT present in the small intestine or the liver is suppressed, elevation of blood cholesterol can be effectively prevented, and a number of studies have heretofore been undertaken regarding ACAT inhibitors.

The present inventors focused on ACAT in vascular wall and studied on the selective inhibitors against this type of ACAT, thus leading to the finding that azole compounds having a cyclic diamine structure, particularly cyclic diamine derivatives of formula (5'):

group, a lower alkoxy lower alkoxy group, a hydroxy lower alkyl group, a hydroxy lower alkoxy group, a lower alkylcarbonyl group, a lower alkylthio group, a lower alkylsulfinyl group, a lower alkylsulfonyl group, a nitro group, or a cyano group, m is 1 or 2, and n is an integer of 1 to 6) or salts thereof exhibit reduced side effects, high water-solubility, and excellent oral absorption property and thus are useful as a remedy for hyperlipidemia and arteriosclerosis. As a result, the present inventors filed a PCT patent application (see WO98/54153 pamphlet).

That patent application discloses a process for preparing cyclic diamine derivatives (5') through the below-described production process 1 (Example 24) or the below-described production process 2 (Example 88). However, there have still been problems in such processes. For example, the following problems are noted: 1) production process 1 requires many steps because of protection and deprotection for an amino group of a piperazine ring; 2) production process 1, and production process 2 which does not use the protective group,

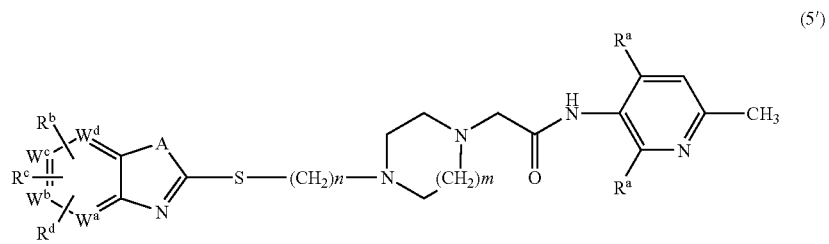

(5')

(wherein A denotes NH, an oxygen atom or a sulfur atom, $W^a$ to $W^d$ denote CH or any one of the $W^a$ to $W^d$ denotes a nitrogen atom, $R^a$ denotes a lower alkylthio group, a lower alkoxy or halo-lower alkoxy group, a lower alkoxy lower alkoxy group, each of $R^b$, $R^c$, and $R^d$ denotes a hydrogen atom, a halogen atom, a lower alkyl group, a lower alkoxy group, a lower alkoxy carbonyl group, a halo-lower alkyl group, a halo-lower alkoxy group, a lower alkoxy lower alkyl have difficulty of synthesizing a cyclic diamine derivative (5') in which the substituent ($R^a$) on the pyridine ring is mono- or di-lower alkyl amino group or a cyclic amino group; and 3) the chlorine atoms in compound (7b) are so highly reactive that the compound substituted by a methoxy group at the 4-position thereof is undesirably produced as a by-product in the reaction process performed in methanol for introducing a lower alkylthio group, and its removal is extremely difficult.

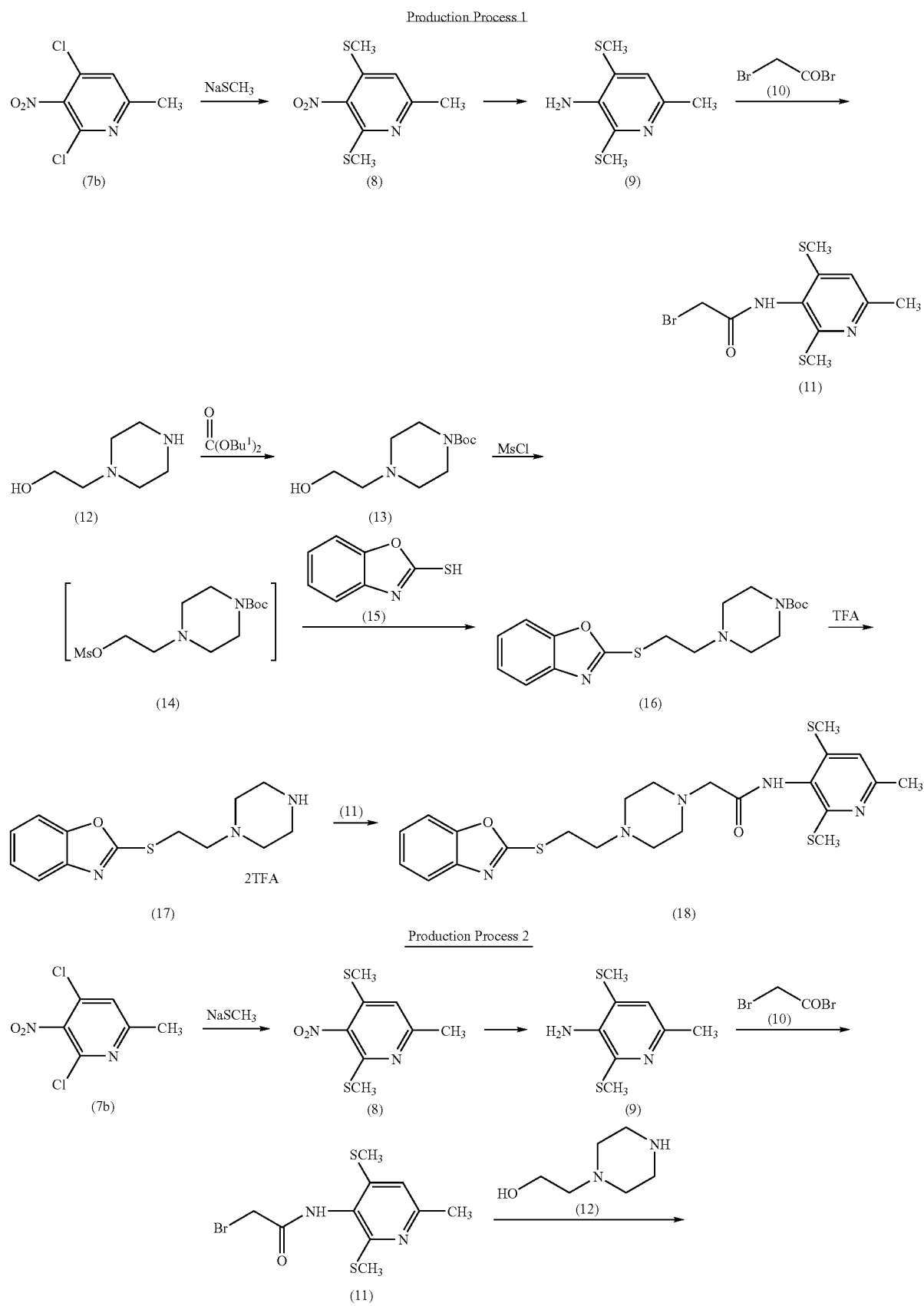

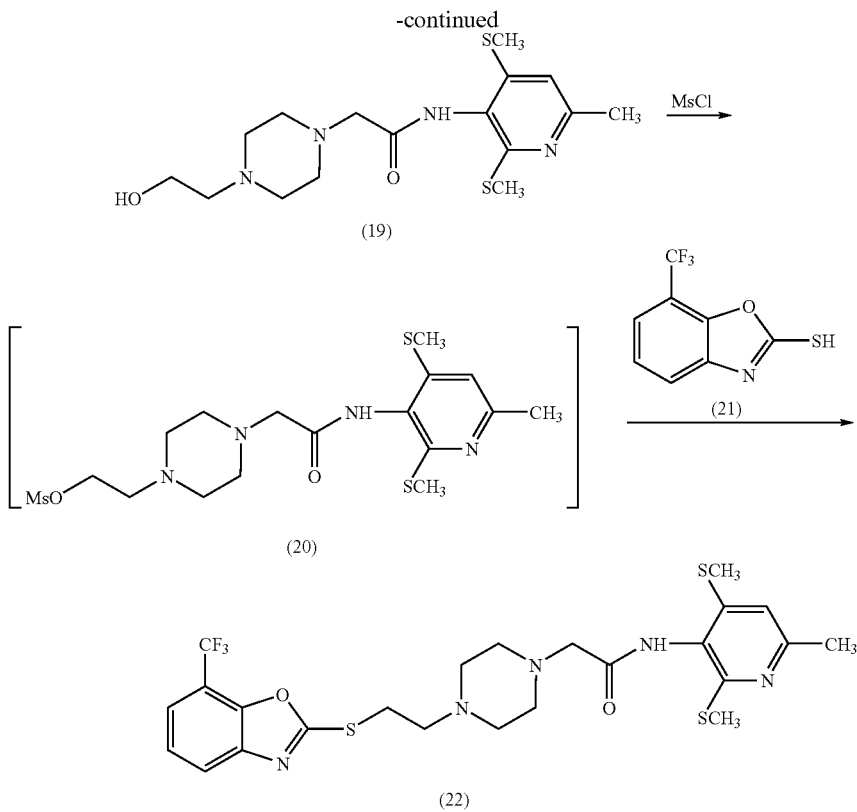

DISCLOSURE OF THE INVENTION

Objects of the present invention include a production intermediate capable of industrially and advantageously synthesizing a cyclic diamine derivative (5), serving as an ACAT inhibitor, or a salt thereof, a process for preparing a cyclic diamine derivative (5) or a salt thereof.

Under the above circumstance, the present inventors have carried out extensive research, and found that, as shown in the below-described reaction scheme, a process which passes a novel hydroxyalkyl cyclic diamine compound (1) which can be obtained from 3-amino-2,4-dihalogeno-6-methylpyridine (7) serving as a starting material, can successfully produce any relevant compound having, as a side chain of the pyridine ring, a mono- or di-lower alkyl amino group or a cyclic amino group, and that a variety of cyclic diamine derivatives (5) or their salts can be produced at a high yield with high purity.

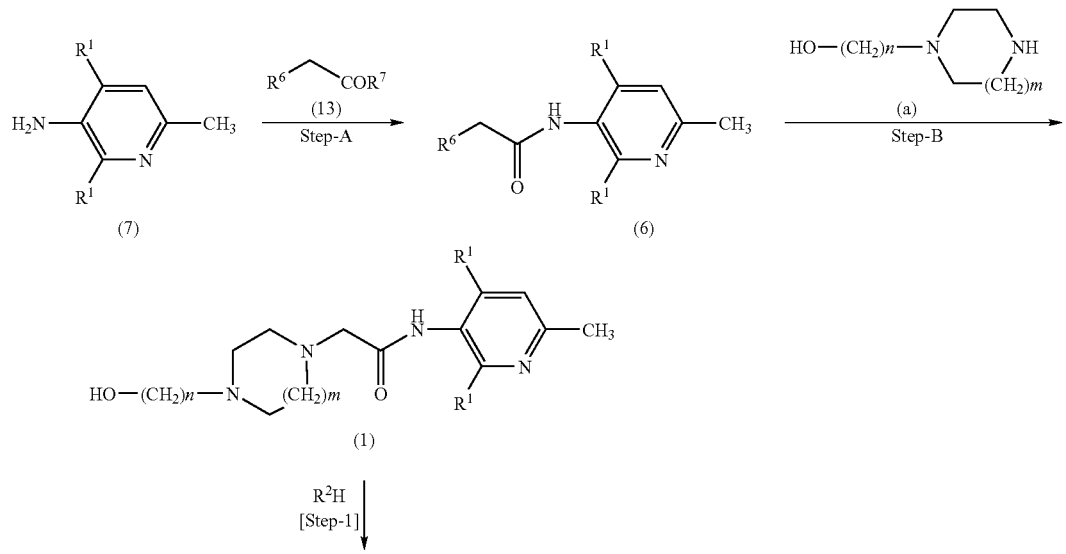

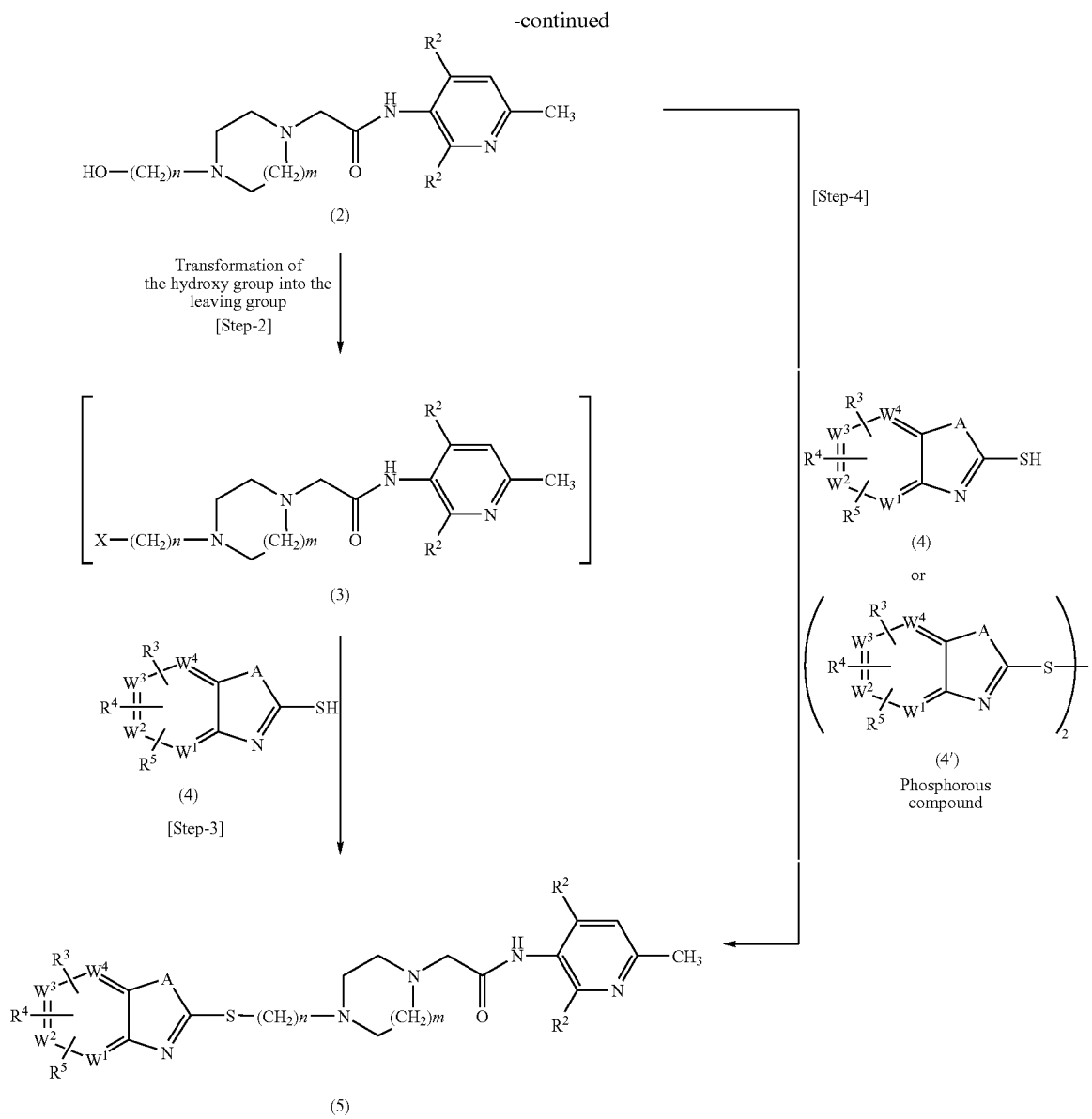

(wherein A denotes NH, an oxygen atom or a sulfur atom, each of $W^1$ to $W^4$ denotes CH or any one of the $W^1$ to $W^4$ denotes a nitrogen atom while the other three of $W^1$ to $W^4$ denotes CH, $R^1$ denotes a halogen atom, $R^2$ denotes a lower alkylthio group, a mono- or di-lower alkylamino group, a cyclic amino group, a lower alkoxy group, a halo-lower alkoxy group, or a lower alkoxy lower alkoxy group, each of $R^3$, $R^4$, and $R^5$ denotes a hydrogen atom, halogen atom, a lower alkyl group, a lower alkoxy group, a lower alkoxycarbonyl group, a halo-lower alkyl group, a halo-lower alkoxy group, a lower alkoxy lower alkyl group, a lower alkoxy lower alkoxy group, a hydroxy lower alkyl group, a hydroxy lower alkoxy group, a lower alkylcarbonyl group, a lower alkylthio group, a lower alkylsulfinyl group, a lower alkylsulfonyl group, a nitro group, or a cyano group, $R^6$ and $R^7$, which may be identical to or different from each other, independently denote a halogen atom, X denotes a leaving group, m is 1 or 2, and n is an integer of 1 to 6).

Accordingly, the present invention provides a hydroxyalkyl cyclic diamine compound of formula (1).

The present invention also provides a process for producing a cyclic diamine derivative of formula (5) or a salt thereof, characterized in that the process comprises reacting a hydroxyalkyl cyclic diamine compound of formula (1) with $R^2H$ to thereby form a compound of formula (2), transforming the hydroxyl group of the compound of formula (2) into a leaving group to thereby form a compound of formula (3) and allowing the compound (3) to react with a thiol derivative of formula (4), or alternatively allowing the compound (2) to react with a thiol derivative of formula (4) or (4') in the presence of a phosphorus compound.

The present invention also provides an acetamide compound of formula (6) and 3-amino-2,4-dibromo-6-methylpyridine of formula (7a), which corresponds to a compound of formula (7) wherein $R^1$ is a bromine atom.

The present invention also provides 2,4-dibromo-6-methyl-3-nitropyridine of formula (24) which is a starting material for producing a compound (7a).

The hydroxyalkyl cyclic diamine compounds of formula (1) according to the present invention are useful intermediates for producing a variety of pharmaceutically useful cyclic diamine derivatives (5) and their salts, and through use of such intermediates, the derivatives can be produced in an industrially advantageous manner with a constant yield.

BEST MODE FOR CARRYING OUT THE INVENTION

Examples of the halogen atom represented by $R^1$, $R^6$, or $R^7$ in the formulae shown in the present specification include a chlorine atom, a bromine atom, and an iodine atom. Of these, a chlorine atom and a bromine atom are preferred.

In the formulae, m is 1 or 2, and n is an integer of 1 to 6. Preferably, m is 1, and n is 2 or 3.

Examples of the lower alkyl groups and the lower alkyl moieties of the lower alkoxy groups represented by $R^2$, $R^3$, $R^4$, or $R^5$ include $C^1$ to C6 alkyl groups which are linear, branched, or cyclic.

Examples of the lower alkylthio groups represented by $R^2$ include a methylthio group, an ethylthio group, a n-propylthio group, an isopropylthio group, a cyclopropylthio group, a cyclopropylmethylthio group, a n-butylthio group and a cyclohexylthio group. Examples of the mono- or di-lower-alkylamino groups represented by $R^2$ include a methylamino group, an ethylamino group, a n-propylamino group, an isopropylamino group, a cyclopropylamino group, a dimethylamino group, a diethylamino group, a di(n-propyl)amino group, a di(isopropyl)amino group and a di(cyclopropyl) amino group. Examples of the cyclic amino groups represented by $R^2$ include a morpholino group, a piperidino group and a pyrrolidinyl group. Examples of the lower alkoxy groups represented by $R^2$ include a methoxy group, an ethoxy group, a n-propoxy group, an isopropoxy group, a n-butoxy group, a cyclopropylmethyloxy group, a cyclopropyloxy group, a cyclohexyloxy group, a cyclopentyloxy group and a cyclobutyloxy group. Examples of the halo-lower alkoxy groups represented by $R^2$ include a difluoromethoxy group, a trifluoromethoxy group and a 2,2,2-trifluoroethoxy group. Examples of the lower alkloxy lower alkoxy groups represented by $R^2$ include a methoxyethoxy group, an ethoxymethoxy group and an ethoxyethoxy group.

Examples of the halogen atoms represented by $R^3$, $R^9$, or $R^5$ include a fluorine atom, a chlorine atom, and a bromine atom. Examples of the lower alkyl groups represented by $R^3$, $R^4$, or $R^5$ include a methyl group, an ethyl group, a n-propyl group, a tert-butyl group and an isopropyl group. Examples of the lower alkoxy groups represented by $R^3$, $R^4$, or $R^5$ include the same groups as mentioned in relation to $R^2$. Examples of the lower alkoxycarbonyl groups represented by $R^3$, $R^4$, or $R^5$ include a methoxycarbonyl group, an ethoxycarbonyl group, a n-propoxycarbonyl group and a tertbutoxycarbonyl group. Examples of the halo-lower alkyl groups represented by $R^3$, $R^4$, or $R^5$ include a trifluoromethyl group and a 2,2,2-trifluoroethyl group. Examples of the halo-lower alkoxy groups represented by $R^3$, $R^4$, or $R^5$ include the same groups as mentioned in relation to $R^2$. Examples of the lower alkoxy lower alkyl groups represented by $R^3$, $R^4$, or $R^5$ include a methoxymethyl group, an ethoxymethyl group and a methoxyethyl group. Examples of the lower alkoxy lower alkoxy groups represented by $R^3$, $R^4$, or $R^5$ include a methoxymethoxy group, an ethoxymethoxy group, a methoxyethoxy group and an ethoxyethoxy group. Examples of the lower hydroxyalkyl groups represented by $R^3$, $R^4$, or $R^5$ include a hydroxymethyl group, a 2-hydroxyethyl group, a 2-hydroxy-2,2-dimethylethyl group and a 3-hydroxy(n-propyl) group. Examples of the lower hydroxy-alkoxy groups represented by $R^3$, $R^4$, or $R^5$ include a 2-hydroxyethoxy group and a 3-hydroxy(n-propoxy) group. Examples of the lower alkylcarbonyl groups represented by $R^3$, $R^4$, or $R^5$ include an acetyl group, a propionyl group and a butyryl group. Examples of the lower alkylthio groups represented by $R^3$, $R^4$, or $R^5$ include a methylthio group, an ethylthio group, a n-propylthio group and an isopropylthio group. Examples of the lower alkylsulfinyl groups represented by $R^3$, $R^4$, or $R^5$ include a methylsulfinyl group, an ethylsulfinyl group, a n-propylsulfinyl group and an isopropylsulfinyl group. Examples of the lower alkylsulfonyl groups represented by $R^3$, $R^4$, or $R^5$ include a methylsulfonyl group, an ethylsulfonyl group, an n-propylsulfonyl group and an isopropylsulfonyl group.

According to the present invention, the cyclic diamine derivative (5) or a salt thereof can be produced from the compound (1) via two or three steps. The individual production steps will next be described.

[Step-1]

The intended compound (2) can be produced by transforming the halogen atoms of a hydroxyalkyl cyclic diamine compound (1) into desired substituents.

(A) Synthesis of thioether compound ($R^2$: a lower alkylthio group)

The thioether compound can be synthesized by adding sodium lower alkylthioalkoxide powder or an organic solvent solution thereof, or an aqueous solution thereof to a solution containing the compound (1) and 18-crown-6.

The sodium lower alkylthioalkoxide is preferably used in an amount of 2.5 to 20 equivalents based on the amount of the compound (1), and 18-crown-6 is preferably used in an amount of 0.05 to 0.5 equivalents based on the amount of the compound (1).

Examples of the solvent include diisopropy alcohol, dimethyl sulfoxide, N,N-dimethylformamide, N-methylpyrrolidone, and toluene. Of these, dimethyl sulfoxide is particularly preferred.

The reaction is preferably performed at a temperature within a range of room temperature to 150° C., more preferably 50 to 110° C. The reaction time is preferably one hour to one day.

(B) Synthesis of amino compound ($R^2$: a mono- or di-lower-alkylamino group, or a cyclic amino group)

The amino compound can be synthesized by adding an amine reagent; i.e., a mono- or di-lower-alkylamine or a cyclic amine to a solution of the compound (1).

The mono- or di-lower-alkylamine or cyclic amine is preferably used in an amount of 5 to 20 equivalents based on the amount of the compound (1).

Examples of the solvent include tetrahydrofuran, toluene, dimethyl sulfoxide, N,N-dimethylfornamide, and N-methylpyrrolidone. The amine reagent can also be employed as the solvent.

The reaction is preferably performed at a temperature within a range of room temperature to 150° C., more preferably 50 to 110° C. The reaction time is preferably 5 hours to 2 days. If necessary, the reaction may be performed in a sealed tube.

(C) Synthesis of ether compound ($R^2$: a lower alkoxy group, a halo-lower alkoxy group, or a lower alkoxy lower alkoxy group)

The ether compound can be synthesized by adding a solution of sodium lower alkoxide, or sodium halo-lower alkloxide, or sodium lower alkoxy lower alkoxide to a solution containing the compound (1) and 18-crown-6.

The sodium lower alkoxide, or sodium halo-lower alkloxide, or sodium lower alkoxy lower alkoxide is preferably used in an amount of 2.5 to 20 equivalents based on the amount of the compound (1), and 18-crown-6 is preferably used in an amount of 0.05 to 0.5 equivalents based on the amount of the compound (1).

Examples of the solvent include tetrahydrofuran, toluene, dimethyl sulfoxide, N,N-dimethylformamide, and N-methylpyrrolidone. Of these, dimethyl sulfoxide is particularly preferred.

The reaction is preferably performed at a temperature within a range of room temperature to 150° C., more preferably 50 to 110° C. The reaction time is preferably one hour to two days.

From the thus-produced compound (2), the compound (5) can be produced through, for example, either of the following routes:

transforming the hydroxyl group of the compound (2) into a leaving group, to thereby form the compound (3), followed by substitution reaction with a thiol derivative (4) (Steps 2 and 3); or reacting the compound (2) with a thiol derivative (4) or (4') using a phosphorus compound (Step 4).

[Step-2]

The compound (3) can be produced by reacting the compound (2) with a reagent which allows transformation from the hydroxyl group into a leaving group; e.g., a sulfonylation agent or a halogenation agent.

No particular limitation is imposed on the type of the leaving groups represented by X so long as the groups can be readily transformed from a hydroxyl group and can be readily substituted by the thiol derivative (4). Examples of the leaving groups include sulfonyloxy groups such as a methanesulfonyloxy group, a chloromethanesulfonyloxy group, an ethanesulfonyloxy group, a propanesulfonyloxy group, a benzenesulfonyloxy group, and a p-toluenesulfonyloxy group; and halogen atoms such as a chlorine atom, a bromine atom, and an iodine atom. Of these, a methanesulfonyloxy group is particularly preferred.

Transformation to a sulfonyloxy group is preferably performed by dissolving the compound (2) in a solvent, adding a sulfonylation agent to the solution, and leading to the reaction for 0.5 to 10 hours in the presence or absence of a base, preferably at 0 to 60° C., more preferably at 0° C. to room temperature.

Examples of preferred sulfonylation agents include methanesulfonyl chloride, methanesulfonic anhydride, benzenesulfonyl chloride, and p-toluenesulfonyl chloride.

Examples of the base include organic bases such as triethylamine, 4-dimethylaminopyridine, N,N-diisopropylethylamine, and pyridine; alkali metal carbonates such as potassium carbonate and sodium carbonate; and alkali metal hydrogencarbonates such as potassium hydrogencarbonate and sodium hydrogencarbonate.

As a solvent, there may be employed tetrahydrofuran, acetonitrile, N,N-dimethylformamide, ethyl acetate, methylene chloride, chloroform, toluene, or dimethyl sulfoxide.

Transformation to a halogen atom is preferably performed by dissolving the compound (2) in a solvent, adding a halogenation agent to the solution, and leading to the reaction for 0.5 to 10 hours in the presence or absence of a base, preferably at 0 to 100° C., more preferably at 0° C. to 60° C.

Examples of the halogenation agents include chlorination agents and bromination agents; e.g., phosphorus oxychloride, phosphorus pentachloride, dichlorotriphenylphosphine, dibromotriphenylphosphine, dichlorotriphenyl phosphite, dibromotriphenyl phosphite, phosphorus tribromide, thionyl chloride, triphenylphosphine and carbon tetrachloride, triphenylphosphine and carbon tetrabromide, and methanesulfonyl chloride and 4-dimethylaminopyridine.

Examples of the solvents which may be used include dichloromethane, chloroform, benzene, toluene, tetrahydrofuran, pyridine, and N,N-dimethylforamide.

[Step-3]

The cyclic diamine derivative (5) can be produced by reacting, in a solvent, the compound (3) with a thiol derivative (4) in the presence or absence of a base and a catalyst.

Examples of the base which may be used include organic bases such as triethylamine, 4-dimethylaminopyridine, N,N-diisopropylethylamine, and pyridine; alkali metal carbonates such as potassium carbonate and sodium carbonate; and alkali metal hydrogencarbonates such as potassium hydrogencarbonate and sodium hydrogencarbonate. Examples of the catalyst include crown ethers such as 18-crown-6 and 15-crown-5; and quaternary ammonium salts such as tetrabutylammonium chloride, tetrabutylammonium bromide, tetrabutylammonium iodide, tetrabutylammonium hydrogensulfate, and benzyltrimethylammonium bromide. Of these, 18-crown-6 is preferred.

Examples of the solvents which may be used include tetrahydrofuran, acetone, acetonitrile, N,N-dimethylformamide, and dimethyl sulfoxide. The reaction is generally performed at 0 to 120° C., preferably at 20 to 100° C. for 0.5 to 10 hours, preferably for 1 to 3 hours.

[Step-4]

Examples of the phosphorus compound employed in Step-4 include phosphine reagents used in Mitsunobu reaction; combined phosphorus reagents containing one of the phosphine reagents and an azo reagent or an ethylenedicarboxylic acid reagent such as dimethyl maleate or N,N,N',N'-tetramethylfumaramide; and phosphonium ylide reagents.

Preferred modes for carrying out Step-4 include (1) reacting the compound (2) with a thiol derivative (4) in the presence of a phosphine reagent and an azo reagent or an ethylenedicarboxylic acid reagent such as dimethyl maleate or N,N,N',N'-tetramethylfumaramide (Method A); (2) reacting the compound (2) with a thiol derivative (4) in the presence of a phosphonium ylide reagent (Method B); (3) reacting the compound (2) with a thiol derivative (4') in the presence of a phosphine reagent (Method C).

<Method A>

Method A can be carried out by dissolving the compound (2), a thiol derivative (4), and a phosphine reagent in a reaction solvent, adding an azo reagent or an ethylenedicarboxylic acid reagent to the solution, and leading to the reaction under argon or nitrogen atmosphere for 2 hours to one day at 0° C. to 100° C., preferably between room temperature and 80° C.

Examples of the phosphine reagent employed in the reaction include trialkylphosphines such as trimethylphosphine, triethylphosphine, tripropylphosphine, triisopropylphosphine, tributylphosphine, triisobutylphosphine, and tricyclohexylphosphine; and triarylphosphine such as triphenylphosphine and diphenylphosphinopolystyrene. Of these, trimethylphosphine, tributylphosphine, and triphenylphosphine are preferred.

Examples of the azo reagents include diethylazodicarboxylic acid (DEAD), 1,1'-azobis(N,N-dimethylfonnamide) (TMAD), 1,1'-(azodicarbonyl)dipiperidine (ADDP), 1,1'-azobis(N,N-diisopropylformamide) (TIPA), and 1,6-dimethyl-1,5,7-hexahydro-1,4,6,7-tetrazocine-2,5-dione (DHTD). Of these, diethylazodicarboxylic acid is particularly preferred.

Examples of the reaction solvents which may be used include dimethylformamide, tetrahydrofuran, dioxane, acetonitrile, nitromethane, acetone, ethyl acetate, benzene, chlorobenzene, toluene, chloroform, and methylene chloride. Of these, dimethylfornamide, tetrahydrofuran, dioxane, acetonitrile are preferred, with dimethylformamide and tetrahydrofuran being particularly preferred.

<Method B>

Method B can be carried out by dissolving the compound (2), a thiol derivative (4), and a phosphonium ylide reagent in a reaction solvent and leading to the reaction under argon or nitrogen atmosphere for 2 hours to 12 hours at room temperature to 120° C., preferably at 80° C. to 100° C.

Examples of the phosphonium ylide reagents which may be used in the reaction include alkanoylmethylenetrialkylphosphorane, alkanoylmethylenetriarylphosphorane, alkoxycarbonylmethylenetrialkylphosphorane, alkoxycarbonylmethylenetriaryl-phosphorane, cyanomethylenetrialkylphosphorane, and cyanomethylene-triarylphosphorane. Examples of the trialkyl include trimethyl, triethyl, tripropyl, triisopropyl, tributyl, triisobutyl, and tricyclohexyl, and examples of the triaryl include triphenyl and diphenylpolystyrene.

Alternatively, the above method may be carried out using a phosphonium halide reagent instead of the phosphonium yilde reagent, to be reacted to the compound (2) and the thiol derivative (4) in the presence of a base.

Examples of the phosphonium halide reagents used in the above case include (cyanomethyl)trialkylphosphonium halide, (cyanomethyl)triarylphosphonium halide, (alkylcarbonylmethyl)trialkylphosphonium halide, (alkylcarbonylmethyl)triarylphosphonium halide, (alkoxycarbonylmethyl)trialkylphosphonium halide, and (alkoxycarbonylmethyl)triarylphosphonium halide.

Among the above phosphonium halide reagents, each of (cyanomethyl)trialkylphosphonium halide and (cyanomethyl)triarylphosphonium halide may be prepared by reacting the corresponding halogenated acetonitrile with the corresponding trialkylphosphine or triarylphosphine (Tetrahedron, Vol. 57, p. 5451-5454, 2001). Similarly, each of the other phosphonium halide reagents may be prepared by reacting the corresponding alkanoylhalomethyl or alkoxycarbonylhalomethyl with the corresponding trialkylphosphine or triarylphosphine.

Examples of the trialkylphosphines and triarylphosphines used in the above case include those mentioned in relation to Method A. Among them, trimethylphosphine, tributylphosphine, and triphenylphosphine are preferred, with trimethylphosphine being particularly preferred.

Examples of the above alkanoyl include fornyl, acetyl, propionyl, and butyryl, with acetyl and propionyl being preferred. Examples of the alkoxy in alkoxycarbonyl include methoxy, ethoxy, propoxy, and butoxy, with methoxy, ethoxy, and butoxy being preferred.

Preferred halogen atoms are a chlorine atom, a bromine atom, and an iodine atom.

Examples of the bases include organic bases such as triethylamine, N,N-diisopropylethylamine, 1,4-diazabicyclo[2.2.2]octane (DABCO), 1,8-diazabicyclo[5.4.0]undec-7-ene (DBU), and 1,5-diazabicyclo[4.3.0]non-5-ene (DEN); and inorganic bases such as potassium carbonate, sodium carbonate, cesium carbonate, lithium carbonate, lithium diisopropylamide, and potassium hexamethyldisilazide. Of these, N,N-diisopropylethylamine, potassium carbonate, lithium diisopropylamide, and potassium hexamethyldisilazide are preferred, with N,N-diisopropylethylamine and potassium carbonate being particularly preferred.

Examples of preferred reaction solvents include dioxane, tetrahydrofuran, toluene, benzene, dimethylformamide, dimethylsulfoxide, acetonitrile, and propionitrile. Of these, propionitrile is particularly preferred.

<Method C>

Method C can be carried out by dissolving the compound (2), a thiol derivative (4'), and a phosphine reagent in the same reaction solvent as employed in Method A and leading to the reaction under argon or nitrogen atmosphere for 2 hours to 2 days at room temperature to 100° C., preferably at 60° C. to 100° C.

In the reaction, the same trialkylphosphines and triarylphosphines as mentioned in relation to Method A are employed the phosphine reagent. Specific examples include trimethylphosphine, triethylphosphine, tripropylphosphine, triisopropylphosphine, tributylphosphine, triisobutylphosphine, tricyclohexylphosphine, triphenylphosphine, diphenylphosphinopolystyrene. Of these, trimethylphosphine, tributylphosphine, and triphenylphosphine are preferred, with trimethylphosphine and triphenylphosphine being particularly preferred.

Notably, the thiol derivatives (4) and (4') can be produced through the aforementioned method disclosed in PCT Patent Publication WO 98/54153 pamphlet or a similar method.

The compound (1) can be produced through, for example, the below-described Step-A and Step-B.

[Step-A]

3-Amino-2,4-dihalogeno-6-methylpyridine (7) is acylated in a solvent by use of an acid halide (7) in the presence of a base, to thereby produce an acetamide compound (6).

Examples of the base include organic bases such as pyridine, triethylamine, N,N-diisopropylethylamine, 4-dimethylaminopyridine, N,N-dimethylaniline, and N,N-diethylaniline; inorganic bases such as alkali metal hydrogencarbonates (e.g., potassium hydrogencarbonate and sodium hydrogencarbonate) and alkali metal carbonates (e.g., potassium carbonate and sodium carbonate).

Examples of the solvents which are preferably employed include methylene chloride, chloroform, 1,2-dichloroethane, acetonitrile, tetrahydrofuran, ethyl acetate, benzene, and toluene. The reaction is preferably performed for 0.5 to one day at 0 to 80° C., more preferably 0° C. to room temperature.

[Step-B]

To a solution of the acetamide compound (6), a 1-(hydroxyalkyl)piperazine (a) is added in the presence or absence of a base, so as to alkylate the amino group of the piperazine (a), whereby the hydroxyalkyl cyclic diamine compound (1) can be produced.

Examples of the bases which can be used include inorganic bases such as alkali metal carbonates (e.g., potassium carbonate and sodium carbonate) and alkali metal hydrogencarbonates (e.g., potassium hydrogencarbonate and sodium hydrogencarbonate); and organic bases such as pyridine, triethylamine, N,N-diisopropylethylamine, 1,8-diazabicyclo[5.4.0]undec-7-ene (DBU), 1,4-diazabicyclo[2.2.2]octane (DABCO), and N,N-dimethylaniline.

As a solvent, acetonitrile, acetone, tetrahydrofuran, N,N-dimethylformamide, etc. may be employed. Alternatively, the above organic solvent containing water can also be used in accordance with needs. Among these solvents, acetonitrile is particularly preferred.

Preferably, the reaction is performed for 0.5 hours to one day at 0 to 80° C., more preferably 0° C. to room temperature.

Notably, both the compound (7) in which $R^1$ is a bromine atom; i.e., 3-amino-2,4-dibromo-6-methylpyridine (7a), and the acetamide compound (6) are novel compounds, which have never been disclosed in any literature.

3-Amino-2,4-dibromo-6-methylpyridine (7a) may be produced from, for example, 2,4-dihydroxy-6-methyl-3-nitropyridine (23) through the following reaction steps. The resultant 2,4-dibromo-6-methyl-3-nitropyridine (24) is also a novel compound.

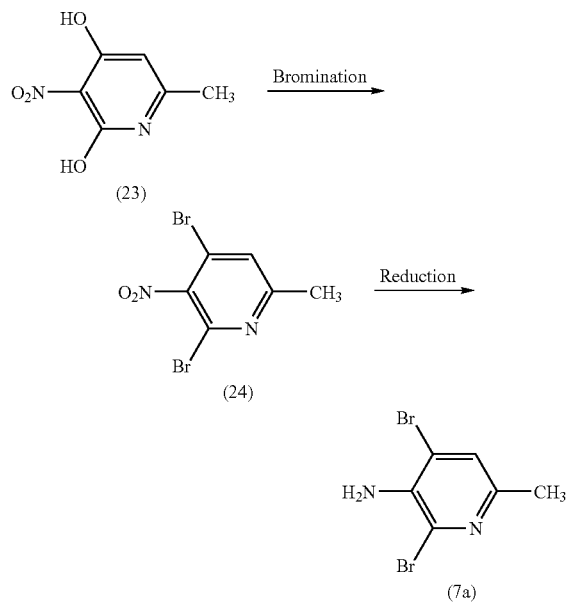

The compound (23); i.e., a dihydroxy species (23), may be brominated by use of a bromination agent in the presence or absence of a base, in a solvent or under solvent-free conditions. Examples of the bromination agents include phosphorus trioxide, phosphorus oxybromide, phosphorus pentabromide, and phosphorus oxybromide-phosphorus pentabromide. Of these, phosphorus oxybromide is preferred. Examples of the bases include N,N-diethylaniline. Examples of the solvents include N,N-dimethylformaldehyde, benzene, chlorobenzene, 1,2-dichloroethane, and dimethyl sulfoxide. The reaction is preferably performed for one to 10 hours at 50 to 150° C., more preferably 100 to 130° C.

The nitro group of the compound (24) can be reduced through, for example, the following methods: reduction by use of a metallic catalyst in the presence of a hydrogen source such as hydrogen gas (Method A); reduction by use of a metal such as zinc (Method B); and reduction by use of a reducing agent such as sodium hydrosulfite ($Na_2S_2O_4$) (Method C).

According to Method A, the nitro group can be reduced in an appropriate solvent in the presence of a hydrogen source such as hydrogen gas, cyclohexadiene, or formic acid and a metallic reduction catalyst such as platinum, palladium, or Raney nickel. Examples of the solvents include alcoholic solvents such as methanol, ethanol, and isopropyl alcohol; solvents such as ethyl acetate, tetrahydrofuran, acetic acid, N,N-dimethylformamide, dioxane, and mixtures thereof; and the above organic solvent containing water. The reaction is preferably performed for 0.5 hours to one day at 0 to 100° C., more preferably room temperature to 80° C.

According to Method B, the nitro group can be reduced in a solvent in the presence of a metallic component such as zinc, iron, tin, or tin(II) chloride. Examples of the solvents include alcoholic solvents such as ethanol and isopropyl alcohol; acetic acid; and the above organic solvent containing water. An acid such as hydrochloric acid or sulfuric acid may also be added in accordance with needs. The reaction is preferably performed for 0.5 hours to one day at 0 to 100° C.

According to Method C, the nitro group can be reduced in a solvent through addition of a sulfur-containing reducing agent such as sodium hydrosulfite, sodium hydrogensulfide, sodium sulfide, or hydrogen sulfide. Of these, sodium hydrosulfite is particularly preferred. Examples of preferred solvents include alcoholic solvents such as methanol, ethanol, and isopropyl alcohol; and aqueous solvents containing tetrahydrofuran, dioxane, or a similar compound. In the reduction, an amine additive such as ammonia, ethylenediamine or propanediamine may be added. The reaction is preferably performed for 0.5 to one day at room temperature to 100° C., more preferably room temperature to 80° C.

EXAMPLES

The present invention will next be described in more detail by way of examples.

Example 1

Synthesis of 2,4-dibromo-6-methyl-3-nitropyridine

In a nitrogen atmosphere, phosphorus oxybromide (58.0 g, 202 mmol) was melted with heat at 65° C., and 2,4-dihydroxy-6-methyl-3-nitropyridine (6.00 g, 35.3 mmol) was added to the melt with stirring. The mixture was heated to 120° C. and stirred for 1 hour. The mixture was allowed to cool and water (100 mL) was added to the mixture, to thereby deactivate excessive phosphorus oxybromide present in the mixture. The mixture was extracted with chloroform. The organic layer was washed with saturated brine, followed by drying over sodium sulfate anhydrate and concentrating under reduced pressure. The residue was purified through silica gel column chromatography (chloroform), to thereby yield 10.29 g of 2,4-dibromo-6-methyl-3-nitropyridine as pale yellow crystals (yield: 98.6%). The product was recrystallized from diethyl ether-hexane, to thereby yield colorless crystals.

m.p.: 118-120° C. IR(KBr)cm$^{-1}$: 1560, 1541, 1439, 1356, 1331. $^1$H-NMR(CDCl$_3$)δ: 2.61(3H, s), 7.46(1H, s). Elementary analysis: as formula $C_6H_4Br_2N_2O_2$ Calculated: C, 24.35; H, 1.36; N, 9.47; Br, 54.00. Found: C, 24.29; H, 1.41; N, 9.44; Br, 54.18.

Example 2

Synthesis of 3-amino-2,4-dibromo-6-methylpyridine 2,4-Dibromo-6-methyl-3-nitropyridine (1.0 g, 3.38 mmol) was dissolved in a mixture of methanol (4 mL) and tetrahydrofuran (6 mL), and a solution of sodium hydrosulfite (3.0 g, 17.23 mmol) in water (7 mL) was added thereto over 5 minutes with stirring at 65° C. Subsequently, the mixture was stirred for 30 minutes at 65° C. To the mixture, a solution of sodium hydrosulfite (3.0 g, 17.23 mmol) in water (7 mL) was further added over 5 minutes, and the mixture was stirred for 30 minutes at 65° C. The resultant mixture was allowed to cool, diluted with water, and then the mixture was extracted with chloroform. The organic layer was washed with saturated brine, followed by drying over sodium sulfate anhydrate and concentrating under reduced pressure, to thereby yield 0.89 g of 3-amino-2,4-dibromo-6-methylpyridine as a colorless solid (yield 99%). The product was crystallized from hexane, to thereby obtain colorless crystals.

m.p.: 93-94° C. IR(KBr)cm$^{-1}$: 3413, 3308, 1609, 1567, 1533. $^1$H-NMR (CDCl$_3$)δ: 2.41 (3H, s), 4.40 (2H, br.s), 7.18 (1H, s). Elementary analysis: as formula C$_6$H$_6$Br$_2$N$_2$ Calculated: C, 27.10; H, 2.27; N, 10.53; Br, 60.09. Found: C, 26.87; H, 2.27; N, 10.51; Br, 59.90.

Example 3

Synthesis of N-[2,4-dibromo-6-methylpyridin-3-yl]-2-bromoacetamide

3-Amino-2,4-dibromo-6-methylpyridine (1.16 g, 4.38 mmol) was dissolved in methylene chloride (10 mL). N,N-dimethylaniline (0.77 g, 6.35 mmol) was added to the solution and then a solution of bromoacetyl bromide (1.03 g, 5.12 mmol) in dichloromethane (2 mL) was added dropwise thereto over 5 minutes with stirring and cooling with ice. After completion of addition, the temperature of the mixture was elevated to room temperature and stirred for 12 hours. The resultant mixture was washed sequentially with water, an aqueous saturated sodium hydrogencarbonate solution, and saturated brine. Subsequently, the mixture was dried over sodium sulfate anhydrate and concentrated under reduced pressure. The residue was crystallized from hexane-acetone, to thereby yield 1.44 g of N-[2,4-dibromo-6-methylpyridin-3-yl]-2-bromoacetamide as colorless crystals (yield 85.3%).

m.p.: 197-199° C. IR(KBr)cm$^{-1}$: 3437, 3195, 1672, 1574, 1546. $^1$H-NMR (CDCl$_3$)δ: 2.54(3H, s), 4.09(2H, s), 7.43(1H, s), 7.91(1H, br.s). Elementary analysis: as formula C$_8$H$_7$Br$_3$N$_2$O Calculated: C, 24.84; H, 1.82; N, 7.24; Br, 61.96. Found: C, 24.86; H, 1.83; N, 7.34; Br, 62.01.

Example 4

Synthesis of N-[2,4-dibromo-6-methylpyridin-3-yl]-2-[4-(2-hydroxyethyl)piperazin-1-yl]acetamide N-[2,4-Dibromo-6-methylpyridin-3-yl]-2-bromoacetamide (1.4 g, 37.3 mmol) was dissolved in acetonitrile (60 mL). 1-(2-Hydroxyethyl)piperazine (0.58 g, 4.48 mmol) was added to the solution with stirring and cooling with ice, and then potassium carbonate (37.5 g, 0.271 mol) was added thereto. The temperature of the mixture was elevated to room temperature, and the mixture was stirred for 24 hours. After completion of reaction, the solvent was removed under reduced pressure. Chloroform and water was added to the residue, and the organic layer was collected from the mixture. The aqueous layer was further extracted with chloroform and the two organic layers were combined together. The combined organic layer was washed with saturated brine, dried over sodium sulfate anhydrate, and concentrated under reduced pressure. The residue was purified through silica gel column chromatography (developer: ammonia-saturated methanol/chloroform=1/20), to thereby obtain 1.613 g of N-[2,4-dibromo-6-methylpyridin-3-yl]-2-[4-(2-hydroxyethyl)piperazin-1-yl]acetamide as an amorphous (yield: 99%).

IR(film) cm$^{-1}$: 3290, 1695, 1607, 1572, 1481. $^1$H-NMR (CDCl$^3$)δ: 2.53(3H, s), 2.59(2H, t, J=5.6 Hz), 2.60-2.70(4H, m), 2.72-2.85 (4H, m), 3.22(2H, s), 3.64(2H, t, J 5.6 Hz), 7.42(1H, s), 8.96(1H, br.s). EIMS m/z (relative intensity): 100(100), 434(Br, Br), 436(Br, $^{81}$Br), 438 ($^{81}$Br, $^{81}$Br) HRMS (C$_{14}$H$_{20}$N$_4$O$_2$Br) Calculated: 433.9952, 435.9932, 437.9912. Found: 433.9948, 435.9949, 437.9929.

Example 5

Synthesis of N-[2,4-dichloro-6-methylpyridin-3-yl]-2-bromoacetamide

The procedure of Example 3 was repeated, except that 3-amino-2,6-dichloro-6-methylpyridine was used instead of 3amino-2,4-dibromo-6-methylpyridine, to thereby yield N-[2,4-dichloro-6-methylpyridin-3-yl]-2-bromoacetamide.

m.p. 184-185° C. IR(KBr)cm$^{-1}$: 3227, 3018, 1672, 1581, 1557, 1519, 1452. $^1$H-NMR (DMSO-d$_6$)δ: 2.53 (3H, s), 4.13 (2H, s), 7.64 (1H, s), 10.40 (1H, br.s). Elementary analysis: formula as C$_8$H$_7$BrCl$_2$N$_2$O Calculated: C; 32.25, H; 2.37, N; 9.40. Found: C; 32.30, H; 2.38, N; 9.36.

Example 6

Synthesis of N-[2,4-dichloro-6-methylpyridin-3-yl]-2-[4-(2-hydroxyethyl)piperazin-1-yl]acetamide The procedure of Example 4 was repeated, except that N-[2,4-dichloro-6-methylpyridin-3-yl]-2-bromoacetamide was used instead of N-[2,4-dibromo-6-methylpyridin-3-yl]-2-bromoacetamide, to thereby yield N-[2,4-dichloro-6-methylpyridin-3-yl]-2-[4-(2-hydroxyethyl)piperazin-1-yl]acetamide.

m.p.: 110-111° C. IR(KBr)cm$^{-1}$: 3304, 3248, 2939, 2824, 1691, 1674, 1581, 1541. $^1$H-NMR(CDCl$_3$)δ: 2.53 (3H, s), 2.60 (2H, t, J=5.3 Hz), 2.592.83 (8H, m), 3.23 (2H, s), 3.64 (2H, t, J=5.3 Hz), 7.24 (1H, s), 8.93 (1H, br.s). Elementary analysis: formula as C$_{14}$H$_{20}$Cl$_2$N$_4$O$_2$.0.1H$_2$0 Calculated: C; 48.17, H; 5.83, N; 16.05, Cl; 20.31. Found: C; 48.02, H; 5.89, N; 16.08, Cl; 20.28.

Example 7

Synthesis of 2-[4-(2-hydroxyethyl)piperazin-1-yl]-N-[2,4-bis(methylthio)-6-methylpyridin-3-yl]acetamide A solution of sodium thiomethoxide (7.0 g, 100 mmol) in dimethyl sulfoxide (100 mL) was added to a solution of N-[2,4-dichloro-6-methylpyridin-3-yl]-2-[4-(2-hydroxyethyl)piperazin-1-yl]acetamide (7.0 g, 20 mmol) and 18-crown-6 (530 mg, 2 mmol) in dimethyl sulfoxide (14 mL). The resulting mixture was stirred for 1 hour at 100° C. The reaction mixture was allowed to cool, and then chloroform and water were added thereto. The organic layer was collected from the mixture, and the aqueous layer was further extracted with chloroform. The organic layers were combined together, and the combined organic layer was washed sequentially with water and saturated brine, followed by drying over sodium sulfate anhydrate. The solvent was removed therefrom. The aqueous layer which had been employed for washing was extracted with chloroform, and the obtained organic layer was washed sequentially with water and saturated brine. Subsequently, the solution was dried over sodium sulfate anhydrate, and the solvent was removed. The combined residue was purified through silica gel column chromatography (developer: chloroform/ammonia-saturated methanol=20/1), to thereby yield 6.68 g of 2-[4-(2-hydroxyethyl)piperazin-1-yl]-N-[2,4-bis(methylthio)-6-methylpyridin-3-yl]acetamide as colorless crystals (yield: 90.1%). The product was recrystallized from ethanol-diethyl ether, to thereby yield the product as colorless needles.

m.p.: 119-120° C. IR (neat): 3335, 2924, 2827, 1688, 1478. $^1$H-NMR (CDCl$_3$)δ: 2.42 (3H, s), 2.50 (3H, s), 2.52 (3H, s), 2.58 (2H, t, J=5.3 Hz), 2.59-2.88 (8H, m), 3.21 (2H, s), 3.64 (2H, t, J=5.3 Hz), 6.70 (1H, s), 8.54 (1H, br s). EIMS m/z (relative intensity):370 (M$^+$), 143 (100) Elementary analysis: formula as C$_{16}$H$_{26}$N$_4$O$_2$S$_2$ Calculated: C; 51.86, H; 7.07, N; 15.12, S; 17.31. Found: C; 51.84, H; 7.00, N; 14.92, S; 17.34.

Example 8

Synthesis of 2-[4-(2-hydroxyethyl)piperazin-1-yl]-N-[2,4-bis(methylthio)-6-methylpyridin-3-yl]acetamide In Example 8, N-[2,4-dibromo-6-methylpyridin-3-yl]-2-[4-(2-hydroxyethyl)piperazin-1-yl]acetamide (10.0 g, 23 mmol) was used instead of N-[2,4-dichloro-6-methylpyridin-3-yl]-2-[4-(2-hydroxyethyl)piperazin-1-yl]acetamide used in Example 7. In a manner similar to that of Example 7, the resulting mixture was stirred for 3 hours at 70° C., followed by post-treatment, to thereby yield 7.79 g of 2-[4-(2-hydroxyethyl)piperazin-1-yl]-N-[2,4-bis(methylthio)-6-methylpyridin-3-yl]acetamide as colorless crystals (yield: 91.8%)

Example 9

Synthesis of 2-[4-(2-hydroxyethyl)piperazin-1-yl]-N-[2,4-bis(methylthio)-6-methylpyridin-3-yl]acetamide A 15% (w/v) aqueous solution (269 mL) of sodium thiomethoxide (576 mmol) was added to a solution of N-[2,4-dichloro-6-methylpyridin-3-yl]-2-[4-(2-hydroxyethyl)piperazin-1-yl]acetamide (10.0 g, 29 mmol) and 18-crown-6 (1.52 g, 5.8 mmol) in dimethyl sulfoxide (200 mL). The resulting mixture was stirred for 5 hours at 100° C. and further stirred for 1 hour at 110° C. The reaction mixture was allowed to cool, and chloroform and water were added thereto. The organic layer was collected, and the aqueous layer was further extracted with chloroform. The combined organic layer was washed sequentially with water and saturated brine, followed by drying over sodium sulfate anhydrate. The solvent was removed therefrom. The aqueous layer which had been employed for washing was extracted with chloroform, and the organic layer was washed sequentially with water and saturated brine. Subsequently, the solution was dried over sodium sulfate anhydrate, and the solvent was removed. The combined residue was purified through silica gel column chromatography (developer: chloroform/ammonia-saturated methanol=20/1), to thereby yield 6.63 g of 2-[4-(2-hydroxyethyl)piperazin-1-yl]-N-[2,4-bis(methylthio)-6-methylpyridin-3-yl]acetamide as colorless crystals (yield: 62.1%).

Example 10

Synthesis of 2-[4-(2-hydroxyethyl)piperazin-1-yl]-N-[2,4-bis(methylthio)-6-methylpyridin-3-yl]acetamide In Example 10, N-[2,4-dibromo-6-methylpyridin-3-yl]-2-[4-(2-hydroxyethyl)piperazin-1-yl]acetamide was used instead of N-[2,4-dichloro-6-methylpyridin-3-yl]-2-[4-(2-hydroxyethyl)piperazin-1-yl]acetamide used in Example 9. In a manner similar to that of Example 9, the resulting mixture was stirred for 2 hours at 100° C., followed by post-treatment, to thereby yield 6.60 g of 2-[4-(2-ydroxyethyl) piperazin-1-yl]-N-[2,4-bis(methylthio)-6-methylpyridin-3-yl]acetamide as colorless crystals (yield: 77.7%).

Example 11

Synthesis of 2-[4-(2-hydroxyethyl)piperazin-1-yl]-N-[2,4-bis(morpholino)-6-methylpyridin-3-yl]acetamide Morpholine (9.0 mL) was added to N-(2,4-dichloro-6-methylpyridin-3-yl)-2-[4-(2-hydroxyethyl)piperazin-1-yl] acetamide (1.0 g, 2.88 mmol), and the mixture was stirred for 24 hours at 100° C. The reaction mixture was allowed to cool and concentrated under reduced pressure. The residue was purified through silica gel column chromatography (developer: chloroform/ammonia-saturated methanol=50/1), to thereby yield 826 mg of 2-[4-(2-hydroxyethyl)piperazin-1-yl]-N-[2,4-bis(morpholino)-6-methylpyridin-3-yl]acetamide in a yellow amorphous state (yield: 63.9%).

$^1$H-NMR(CDCl$_3$)δ: 2.41(3H, s), 2.50-2.80 (10H, m), 3.00 (4H, t, J=4.5 Hz), 3.12(4H, t, J=4.5 Hz), 3.18(2H, s), 3.55-3.80(10H, m), 6.50(1H, s), 8.52(1H, br.s)

Example 12

Synthesis of 2-[4-[2-(benzimidazol-2-ylthio)ethyl]piperazin-1-yl]-N-[2,4-bis(methylthio)-6-methylpyridin-3-yl]acetamide 2-[4-(2-Hydroxyethyl)piperazin-1-yl]-N-[2,4-bis(methylthio)-6-methylpyridin-3-yl]acetamide (104.94 g, 0.286 mol) was dissolved in tetrahydrofuran (1.4 L), and triethylamine (48.5 g, 0.479 mol), 4-dimethylaminopyridine (1.76 g, 14.4 mmol), and methanesulfonyl chloride (42 g, 0.366 mol) were sequentially added to the solution under cooling with ice, followed by stirring for 1 hour at the same temperature. The reaction mixture was filtered, and the filtrate was concentrated under reduced pressure, to thereby yield 144.92 g of a pale yellow foamed substance. The product was dissolved in N,N-dimethylformamide (1 L), and 2-mercaptobenzimidazole (48.58 g, 0.323 mol), potassium carbonate (48.58 g, 0.351 mol), and 18-crown-6 (3.56 g, 13.5 mmol) were added to the resultant solution at room temperature, followed by stirring for 3 hours at 80° C. The reaction mixture was concentrated under reduced pressure, and the residue was partitioned by adding chloroforn and water. The aqueous layer was extracted with chloroform. The combined organic layer was washed with saturated brine, dried over sodium sulfate anhydrate, and concentrated under reduced pressure. The residue was purified through silica gel column chromatography (developer: hexane/acetone=1/1-1/3), to thereby yield 55.85 g of 2-[4-[2-(benzimidazol-2-ylthio)ethyl]piperazin-1-yl]-N-[2,4-bis(methylthio)-6-methylpyridin-3-yl]acetamide (yield: 39.2%).

Example 13

Synthesis of 2-[4-[2-(7-trifluoromethylbenzoxazol-2-ylthio)ethyl]piperazin-1-yl]-N-[2,4-bis(methylthio)-6-methylpyridin-3-yl]acetamide The reaction and treatments of Example 12 were repeated, except that 2-mercaptobenzimidazole was replaced by 2-mercapto-7-trifluoromethylbenzoxazole, to thereby yield the title compound as colorless needles.

m.p.: 155-156° C. (decomposition)

Example 14

Synthesis of 2-[4-[2-(benzoxazol-2-ylthio)ethyl]piperazin-1-yl]-N-[2,4-bis(methylthio)-6-methylpyridin-3-yl]acetamide The reaction and treatments of Example 12 were repeated, except that 2-mercaptobenzimidazole was replaced by 2-mercaptobenzoxazole, to thereby yield the title compound as colorless needles.

m.p.: 140-142° C.

Example 15

Synthesis of 2-[4-(2-hydroxyethyl)piperazin-1-yl]-N-[2,4-bis(2,2,2-trifluoroethoxy)-6-methylpyridin-3-yl]acetamide Sodium hydride (1.26 g) was added to 2,2,2-trifluoroethanol (12 mL) under cooling with ice, and the mixture was stirred for 10 minutes at the same temperature. A solution of N-[2,4-dichloro-6-methylpyridin-3-yl]-2-[4-(2-hydroxyethyl)piperazin-1-yl]acetamide (2.00 g, 5.76 mmol) in dimethyl sulfoxide (80 mL) was added to the reaction mixture, and the resultant mixture was stirred for 24 hours at 100° C. The reaction mixture was allowed to cool, and ethyl acetate and water were added to the mixture. The organic layer was separated, and the aqueous layer was extracted with ethyl acetate. The combined organic layers were washed sequentially with water and saturated brine, and dried over sodium sulfate anhydrate. The solvent was removed under reduced pressure, and the residue was purified through silica gel column chromatography (developer: chloroform/ammonia saturated methanol=200/3), to thereby yield 2.35 g of 2-[4-(2-hydroxyethyl)piperazin-1-yl]-N-[2,4-bis(2,2,2-trifluoroethoxy)-6-methylpyridin-3-yl]acetamide (yield: 86.0%) as yellow crystals.

$^1$H-NMR(CDCl$^3$)δ: 2.42 (3H, s), 2.48-2.82 (10H, m), 3.17 (2H, s), 3.63 (2H, t, J=5.4 Hz), 4.41 (2H, q, J=8.0 Hz), 4.75 (2H, q, J=8.5 Hz), 6.47 (1H, s), 8.38 (1H, br.s).

Example 16

Synthesis of 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide.

The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(2,2,2-trifluoroethoxy)-6-methylpyridin-3-yl]acetamide, and 2-mercaptobenzimidazole was replaced by 5,6-difluoro-2-mercaptobenzimidazole, to thereby yield the title compound as a colorless foamed substance.

$^1$H-NMR (CDCl$_3$)δ: 2.42 (3H, s), 2.50-3.05 (10H, m), 3.25 (2H, t, J=5.3 Hz), 3.31 (2H, s), 4.42 (2H, q, J=8.0 Hz), 4.75 (2H, q, J=8.5 Hz), 6.46 (1H, s), 7.12 (1H, br.s), 7.41 (1H, br.s), 8.26 (1H, s), 13.20 (1H, br.s).

Example 17

Synthesis of 2-[4-[2-(5-fluorobenzimidazol-2-ylthio)ethyl]piperazin-1-yl]-N-[2,4-bis(2,2,2-trifluoroethoxy)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl) piperazin-1-yl]-N-[2, 4-bis(2,2,2-trifluoroethoxy)-6-methylpyridin-3-yl]acetamide, and 2-mercaptobenzimidazole was replaced by 5-fluoro-2-mercaptobenzimidazole, to thereby yield the title compound as a pale brown foamed substance.

$^1$H-NMR(CDCl$_3$)δ: 2.41 (3H, s), 2.66-2.91 (8H, m), 2.97 (2H, t, J=5.1 Hz), 3.25 (2H, t, J=5.1 Hz), 3.29 (2H, s), 4.41 (2H, q, J=8.0 Hz), 4.75 (2H, q, J=8.5 Hz), 6.45 (1H, s), 6.93 (1H, td, J=9.0, 2.3 Hz), 7.10-7.56 (2H, m), 8.28 (1H, s), 13.14 (1H, br.s).

Example 18

Synthesis of 2-[4-[2-(benzoxazol-2-ylthio)ethyl]piperazin-1-yl]-N-[2,4-bis(2,2,2-trifluoroethoxy)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(2,2,2-trifluoroethoxy)-6-methylpyridin-3-yl]acetamide, and 2-mercaptobenzimidazole was replaced by 2-mercaptobenzoxazole, to thereby yield the title compound as a colorless crystalline powder.

$^1$H-NMR(CDCl$_3$)δ: 2.42 (3H, s), 2.54-2.76 (8H, m), 2.84 (2H, t, J=6.9 Hz), 3.15 (2H, s), 3.49 (2H, t, J=6.9 Hz), 4.41 (2H, q, J=8.0 Hz), 4.75 (2H, q, J=8.5 Hz), 6.46 (1H, s), 7.25-7.35 (2H, m), 7.43 (1H, d, J=7.8 Hz), 7.59 (1H, d, J=7.8 Hz), 8.38 (1H, s).

Example 19

Synthesis of 2-[4-[2-(benzimidazol-2-ylthio)ethyl]piperazin-1-yl]-N-[2,4-bis(2,2,2-trifluoroethoxy)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(2,2,2-trifluoroethoxy)-6-methylpyridin-3-yl]acetamide, to thereby yield the title compound as a colorless crystalline powder.

$^1$H-NMR(CDCl$_3$)δ: 2.43 (3H, s), 2.65-2.97 (8H, m), 3.01 (2H, t, J=5.0 Hz), 3.23 (2H, t, J=5.0 Hz), 3.31 (2H, s), 4.42 (2H, q, J=8.0 Hz), 4.75 (2H, q, J=8.5 Hz), 6.48 (1H, s), 7.6-7.24 (2H,m), 7.41-7.65 (2H, m), 8.26 (1H, s).

Example 20

Synthesis of 2-[4-[2-(5-chloro-7-isopropyl-4-methylbenzoxazol-2-ylthio)ethyl]piperazin-1-yl]-N-[2,4-bis(2,2,2-trifluoroethoxy)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4 bis(2,2,2-trifluoroethoxy)-6-methylpyridin-3-yl]acetamide, and 2-mercaptobenzimidazole was replaced by 5-chloro-7-isopropyl-2-mercapto-4-methylbenzoxazole, to thereby yield the title compound as a colorless crystalline powder.

$^1$H-NMR(CDCl$_3$)δ: 1.32 (6H, d, J=6.9 Hz), 2.42 (3H, s), 2.52 (3H, s), 2.56-2.78 (8H, m), 2.85 (2H, t, J=7.0 Hz), 3.15 (2H, s), 3.22 (1H, sept, J=6.9 Hz), 3.48 (2H, t, J=7.0 Hz), 4.41 (2H, q, J=8.0 Hz), 4.74 (2H, q, J=8.5 Hz), 6.46 (1H, s), 7.07 (1H, s), 8.37 (1H, s).

Example 21

Synthesis of 2-[4-(2-hydroxyethyl)piperazin-1-yl]-N-[2,4-dimethoxy-6-methylpyridin-3-yl]acetamide The reaction and treatments of Example 7 were repeated, except that sodium thiomethoxide was replaced by sodium methoxide, to thereby yield the title compound as a colorless crystalline powder.

$^1$H-NMR(CDCl$_3$)δ: 2.42 (3H, s), 2.48-2.83 (10H, m), 3.17 (2H, s), 3,64 (2H, t, J=5.3 Hz), 3.83 (3H, s), 3.91 (3H, s), 6.43 (1H, s), 8.26 (1H, br.s).

Example 22

Synthesis of 2-[4-[2-(benzoxazol-2-ylthio)ethyl]piperazin-1-yl]-N-[2,4-dimethoxy-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-dimethoxy-6-methylpyridin-3-yl]acetamide, and 2-mercaptobenzimidazole was replaced by 2-mercaptobenzoxazole, to thereby yield the title compound as a colorless crystalline powder.

$^1$H-NMR (CDCl$_3$)δ: 2.42 (3H, s), 2.54-2.76 (8H, m), 2.84 (2H, t, J=7.0 Hz), 3.16 (2H, s), 3.49 (2H, t, J=7.0 Hz), 3.83 (3H, s), 3.91 (3H, s), 6.42 (1H, s), 7.20-7.31 (2H, m), 7.417.46 (1H, m), 7.56-7.61 (1H, m), 8.25 (1H, br.s).

Example 23

Synthesis of 2-[4-[2-(benzimidazol-2-ylthio)ethyl]piperazin-1-yl]-N-[2,4-bis(1-methylethoxy)-6-methylpyridin-3-yl]acetamide The reaction and treatments of Example 7 were repeated, except that sodium thiomethoxide was replaced by sodium isopropoxide, to thereby yield 2-[4-(2-hydroxyethyl)piperazin-1-yl]-N-[2,4-bis(1-methylethoxy)-6-methylpyridin-3-yl]acetamide as a colorless crystalline powder.

The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(1-methylethoxy)-6-methylpyridin-3-yl]acetamide, to thereby yield the title compound as a colorless foamed substance.

$^1$H-NMR(CDCl$_3$)δ: 1.28 (6H, d, J=6.3 Hz), 1.32 (6H, d, J=6.1 Hz), 2.38 (3H, s), 2.58-3.22 (10H, m), 3.23 (2H, t, J=5.0 Hz), 3.29 (2H, s), 4.58 (1H, sept, J=6.1 Hz), 5.34 (1H, sept, J=6.3 Hz), 6.35 (1H, s), 7.18-7.22 (2H, m), 7.30-7.75 (2H, m), 7.99 (1H, br s).

Example 24

Synthesis of 2-[4-[2-(benzoxazol-2-ylthio)ethyl]piperazin-1-yl]-N-[2,4-bis(1-methylethoxy)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(1-methylethoxy)-6-methylpyridin-3-yl]acetamide and 2mercaptobenzimidazole was replaced by 2-mercaptobenzoxazole, to thereby yield the title compound as a pale yellow viscous oil.

$^1$H-NMR (CDCl$_3$)δ: 1.28 (6H, d, J=6.1 Hz), 1.32 (6h, J=6.1 Hz), 2.37 (3H, s), 2.49-2.78 (8H, m), 2.84 (2H, t, J=7.0 Hz), 3.13 (2H, s), 3.49 (2H, t, J=7.0 Hz), 4.58 (1H, sept, J=6.1 Hz), 5.33 (1H, sept, J=6.1 Hz), 6.34 (1H, s), 7.17-7.31 (2H, m), 7.43 (1H, d, J=6.8 Hz), 7.58 (1H, d, J 7.3 Hz), 8.11 (1H, br.s).

Example 25

Synthesis of 2-[4-[2-(oxazolo[4,5-b]pyridin-2-ylthio)ethyl]piperazin-1-yl]-N-[2,4-bis(1-methylethoxy)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(1-methylethoxy)-6-methylpyridin-3-yl]acetamide, and 2-mercaptobenzimidazole was replaced by 2-mercaptooxazolo[4,5-b]pyridine, to thereby yield the title compound as a yellow oil.

$^1$H-NMR(CDCl$_3$)δ: 1.28 (6H, d, J=6.2 Hz), 1.32 (6h, J=6.1 Hz), 2.37 (3H, s), 2.49-2.82 (8H, m), 2.87 (2H, t, J=6.9 Hz), 3.14 (2H, s), 3.56 (2H, t, J=6.9 Hz), 4.58 (1H, sept, J=6.1 Hz), 5.32 (1H, sept, J=6.2 Hz), 6.34 (1H, s), 7.80 (2H, dd, J=8.0, 4.9 Hz), 7.69 (1H, dd, J=8.0, 1.5 Hz), 8.11 (1H, br.s), 8.46 (1H, dd, J=4.9, 1.5 Hz).

Example 26

Synthesis of 2-[4-(2-hydroxyethyl)piperazin-1-yl]-N-[2,4-bis(pyrrolidin-1-yl)-6-methyl-3-pyridyl]acetamide 2-[4-(Hydroxyethyl)piperazin-1-yl]-N-[2,4-dibromo-6-methyl-3-pyridyl]acetamide (1.00 g, 2.29 mmol) was dissolved in pyrrolidine (10 mL), and the solution was subjected to reflux for 4 days. The reaction mixture was concentrated under reduced pressure, and the residue was subjected to separation through silica gel column chromatography (developer: hexane:acetone=2:1), to thereby yield a crude product of 2-[4-(2-hydroxyethyl)piperazin-1-yl]-N-[2,4-bis(pyrrolidin-1-yl)-6-methyl-3-pyridyl]acetamide (1.22 g) as a brown foamed substance. The crude product was dissolved in pyridine (20 mL), and acetic anhydride (10 mL) was added thereto under cooling with ice, followed by stirrng for 14 hours at room temperature. The reaction mixture was concentrated under reduced pressure. Toluene (70 mL) was added to the residue and then evaporated three times, followed by purification through silica gel column chromatography (developer: chloroform:methanol=20:1→chloroform: ammonia-saturated methanol=50:1→chloroform:ammonia-saturated methanol=20:1), to thereby yield a brown oil (1.05 g). The oil was dissolved in ammonia-saturated methanol (30 mL), and the solution was stirred for 14 hours at room temperature. The reaction mixture was concentrated under reduced pressure, and the residue was purified through silica gel column chromatography (developer: chloroform:ammonia-saturated methanol=100:1→chloroform:ammonia-saturated methanol=20:1), to thereby yield 2-[4-(2-hydroxyethyl) piperazin-1-yl]-N-[2,4-bis(pyrrolidin-1-yl)-6-methyl-3-pyridyl]acetamide (911 mg, yield 95%) as a pale brown foamed substance.

$^1$H-NMR(CDCl$_3$)δ: 1.75-2.05 (8H, m), 2.31 (3H, s), 2.50-2.75 (10H, m), 3.18 (2H, s), 3.25-3.55 (8H, m), 3.63 (2H, t, J=5.2 Hz), 6.04 (1H, s), 8.36 (1H, br.s).

Example 27

Synthesis of 2-[4-[2-(benzimidazol-2-ylthio)ethyl] piperazin-1-yl]-N-[2,4-bis(pyrrolidin-1-yl)-6-methyl-3-pyridyl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(pyrrolidin-1-yl)-6-methylpyridin-3-yl]acetamide, to thereby yield the title compound as a pale yellow foamed substance.

$^1$H-NMR (DMSO-d$_6$, 120° C.)δ: 1.72-1.87 (8H, m), 2.19 (3H, s), 2.33-2.65 (8H, m), 2.74 (2H, m), 3.05 (2H, br.s), 3.26-3.45 (10H, m), 5.99 (1H, s), 7.07-7.12 (2H, m), 7.37-7.45 (2H, m), 8.41 (1H, br.), 12.17 (1H, br.).

Example 28

Synthesis of 2-[4-[2-(benzoxazol-2-ylthio)ethyl] piperazin-1-yl]-N-[2,4-bis(pyrrolidin-1-yl)-6-methyl-3-pyridyl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(pyrrolidin-1-yl)-6-methylpyridin-3-yl]acetamide, and 2-mercaptobenzimidazole was replaced by 2-mercaptobenzoxazole, to thereby yield the title compound as a pale yellow solid.

$^1$H-NMR(DMSO-d$_6$, 120° C.)δ: 1.71-1.88 (8H, m), 2.19 (3H, s), 2.43-2.64 (8H, m), 2.78 (2H, m), 3.03 (2H, br.s), 3.26-3.42 (8H, m), 3.47 (2H, m), 5.99 (1H, s), 7.26-7.34 (2H, m), 7.54.7.61 (2H, m), 8.40 (1H, br.)

Example 29

Synthesis of 2-[4-[2-(oxazolo[4,5-b]pyridin-2-ylthio) ethyl]piperazin-1-yl]-N-[2,4-bis(pyrrolidin-1-yl)-6-methylpyridin-3-yl]acetamide:

The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(pyrrolidin-1-yl)-6-methylpyridin-3-yl]acetamide, and 2-mercaptobenzimidazole was replaced by 2-mercaptooxazolo[4,5-b]pyridine, to thereby yield the title compound as a pale yellow oil.

$^1$H-NMR (DMSO-d$_6$, 120° C.)δ: 1.72-1.87 (8H, m), 2.19 (3H, s), 2.43-2.64 (8H, m), 2.81 (2H, m), 3.03 (2H, br.s), 3.26-3.44 (8H, m), 3.53 (2H, m), 5.99 (1H, s), 7.30 (1H, m), 7.96 (1H, m), 8.36-8.44 (2H, m).

Example 30

Synthesis of 2-[4-[2-(7-trifluoromethylbenzoxazol-2-ylthio)ethyl]piperazin-1-yl]-N-[2,4-bis(pyrrolidin-1-yl)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(pyrrolidin-1-yl)-6-methylpyridin-3-yl]acetamide, and 2-mercaptobenzimidazole was replaced by 2-mercapto-7-trifluoromethylbenzoxazole, to thereby yield the title compound as a pale yellow oil.

$^1$H-NMR (DMSO-d$_6$, 120° C.)δ: 1.72-1.90 (8H, m), 2.19 (3H, s), 2.43-2.61 (8H, m), 2.80 (2H, m), 3.02 (2H, br.s), 3.26-3.45 (8H, m), 3.51 (2H, m), 6.00 (1H, s), 7.51 (1H, t, J=7.8 Hz), 7.60 (1H, d, J=7.8 Hz), 7.89 (1H, d, J=7.8 Hz), 8.41 (1H, br.).

Example 31

Synthesis of 2-[4-[2-(5-chloro-7-isopropyl-4-methyl-benzoxazol-2-ylthio)ethyl]piperazin-1-yl]-N-[2,4-bis (pyrrolidin-1-yl)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(pyrrolidin-1-yl)-6-methyl-3-pyridyl]acetamide, and 2-mercaptobenzimidazole was replaced by 2-mercapto-5-chloro-7-isopropyl-4-methylbenzoxazole, to thereby yield the title compound as a pale yellow oil.

$^1$H-NMR(DMSO-d$_6$, 120° C.)δ: 1.33 (6H, d, J=6.8 Hz), 1.72-1.90 (8H, m), 2.21 (3H, s), 2.44-2.64 (8H, m), 2.80 (2H, m), 3.05 (2H, br.s), 3.23 (1H, sept, J=6.8 Hz), 3.27-3.46 (8H, m), 3.48 (2H, m), 6.02 (1H, s), 7.16 (1H, s), 8.46 (1H, br.)

Example 32

Synthesis of 2-[4-[2-(benzothiazol-2-ylthio)ethyl] piperazin-1-yl]-N-[2,4-bis(pyrrolidin-1-yl)-6-methyl-3-pyridyl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(pyrrolidin-1-yl)-6-methylpyridin-3-yl]acetamide, and 2-mercaptobenzimidazole was replaced by 2-mercaptobenzothiazole, to thereby yield the title compound as a pale yellow solid.

$^1$H-NMR(DMSO-d$_6$, 120° C.)δ: 1.71-1.88 (8H, m), 2.19 (3H, s), 2.44-2.63 (8H, m), 2.78 (2H, m), 3.04 (2H, br.s), 3.26-3.44 (8H, m), 3.50 (2H, m), 5.99 (1H, s), 7.34 (1H, t, J=7.6 Hz), 7.45 (1H, t, J=7.6 Hz), 7.82 (1H, d, J=7.6 Hz), 7.94 (1H, d, J=7.6 Hz), 8.41 (1H, br.)

Example 33

Synthesis of 2-[4-[2-(benzimidazol-2-ylthio)ethyl]piperazin-1-yl]-N-[2,4-bis(morpholino)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(morpholino)-6-methylpyridin-3-yl]acetamide, to thereby yield the title compound as a colorless crystalline powder.

$^1$H-NMR(CDCl$_3$)δ: 2.42 (3H, s), 2.74-2.94 (8H, m), 2.95-3.06 (6H, m), 3.07-3.21 (4H, m), 3.23-3.40 (4H, m), 3.68-3.88 (8H, m), 6.52 (1H, s), 7.14-7.26 (2H, m), 7.44-7.63 (2H, m), 8.41 (1H, s)

Example 34

Synthesis of 2-[4-[2-(benzoxazol-2-ylthio)ethyl]piperazin-1-yl]-N-[2,4-bis(morpholino)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4 bis(morpholino)-6-methylpyridin-3-yl]acetamide, and 2-mercaptobenzimidazole was replaced by 2-mercaptobenzoxazole, to thereby yield the title compound as a colorless foamed substance.

$^1$H-NMR(CDCl$_3$)δ: 2.41 (3H, s), 2.58-2.78 (8H, m), 2.86 (2H, t, J=6.9 Hz), 2.94-3.04 (4H, m), 3.06-3.15 (4H, m), 3.16 (2H, s), 3.49 (2H, t, J=6.9 Hz), 3.68-3.82 (8H, m), 6.50 (1H, s), 7.20-7.32 (2H, m), 7.44 (1H, d, J=7.2 Hz), 7.59 (1H, d, J=7.2 Hz), 8.54 (1H, s).

Example 35

Synthesis of 2-[4-[2-(oxazolo[4,5-b]pyridin-2-ylthio)ethyl]piperazin-1-yl]-N-[2,4-bis(morpholino)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(morpholino)-6-methylpyridin-3-yl]acetamide, and 2-mercaptobenzimidazole was replaced by 2-mercaptooxazolo[4,5-b]pyridine, to thereby yield the title compound as a colorless foamed substance.

$^1$H-NMR(CDCl$_3$)δ: 2.41 (3H, s), 2.62-2.78 (8H, m), 2.89 (2H, t, J=6.7 Hz), 3.01 (4H, t, J=4.6 Hz), 3.12 (4H, t, J=4.6 Hz), 3.17 (2H, s), 3.56 (2H, t, J=6.7 Hz), 3.70-3.80 (8H, m), 6.50 (1H, s), 7.19 (1H, dd, J=8.0, 5.0 Hz), 7.70 (1H, dd, J=8.0, 1.5 Hz), 8.46 (1H, dd, J=5.0, 1.5 Hz), 8.53 (1H, s)

Example 36

Synthesis of 2-[4-[2-(7-trifluoromethylbenzoxazol-2-ylthio)ethyl]piperazin-1-yl]-N-[2,4-bis(morpholino)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(morpholino)-6-methylpyridin-3-yl]acetamide, and 2-mercaptobenzimidazole was replaced by 2-mercapto-7-trifluoromethylbenzoxazole, to thereby yield the title compound as a colorless foamed substance.

$^1$H-NMR (CDCl$_3$)δ: 2.41 (3H, s), 2.58-2.77 (8H, m), 2.87 (2H, t, J=6.8 Hz), 2.94-3.05 (4H, m), 3.06-3.19 (6H, m), 3.52 (2H, t, J=6.8 Hz), 3.72-3.82 (8H, m), 6.50 (1H, s), 7.38 (1H, t, J=7.8 Hz), 7.48 (1H, d, J=7.8 Hz), 7.76 (1H, d, J=7.8 Hz), 8.53 (1H, s).

Example 37

Synthesis of 2-[4-[2-(5-chloro-7-isopropyl-4-methylbenzoxazol-2-ylthio)ethyl]piperazin-1-yl]-N-[2,4-bis(morpholino)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(morpholino)-6-methylpyridin-3-yl]acetamide, and 2-mercaptobenzimidazole was replaced by 2-mercapto-5-chloro-7-isopropyl-4'-methylbenzoxazole, to thereby yield the title compound as a colorless foamed substance.

$^1$H-NMR(CDCl$_3$)δ: 1.33 (6H, d, J=6.8 Hz), 2.41 (3H, s), 2.52 (3H, s), 2.57-2.79 (8H, m), 2.87 (2H, t, J=6.9 Hz), 3.00 (4H, t, J=4.4 Hz), 3.12 (4H, t, J=4.4 Hz), 3.16 (2H, s), 3.23 (1H, sept, J=6.8 Hz), 3.49 (2H, t, J=6.9 Hz), 3.66-3.84 (8H, m), 6.50 (1H, s), 7.08 (1H, s), 8.53 (1H, s)

Example 38

Synthesis of 2-[4-[2-(benzothiazol-2-ylthio)ethyl]piperazin-1-yl]-N-[2,4-bis(morpholino)-6-methylpyridin-3-yl]acetamide The reaction and treatments of Example 12 were repeated, except that 2-[4-(2-hydroxyethyl)piperazin-1-yl]-N-[2,4-bis(methylthio)-6-methylpyridin-3-yl]acetamide was replaced by 2-[4-(2-hydroxyethyl)piperazin-1-yl]-N-[2,4-bis(morpholino)-6-methylpyridin-3-yl]acetamide, and 2-mercaptobenzimidazole was replaced by 2-mercaptobenzothiazole, to thereby yield the title compound as a colorless foamed substance.

$^1$H-NMR (CDCl$_3$)δ: 2.40 (3H, s), 2.59-2.77 (8H, m), 2.86 (2H, t, J=7.0 Hz), 3.00 (4H, t, J=4.5 Hz), 3.12 (4H, t, J=4.5 Hz), 3.16 (2H, m), 3.54 (2H, t, J=7.0 Hz), 3.70-3.82 (8H, m), 6.50 (1H, s), 7.30 (1H, dt, J=7.7, 1.1 Hz), 7.41 (1H, dt, J=7.7, 1.1 Hz), 7.76 (1H, d, J=7.7, Hz), 7.85 (1H, d, J=7.7, Hz), 8.53 (1H, s).

Production Example 1

Synthesis of 3-amino-2,4-dichloro-6-methylpyridine 2,4-Dichloro-6-methyl-3-nitropyridine (30 g, 144.9 mmol) was dissolved in ethanol (300 mL), and Raney nickel (1.50 g, 25.6 mmol) was added to the solution, followed by stirring for 7 hours at 60° C. under hydrogen atmosphere(0.15 MPa). Raney nickel was removed through filtration, and the filtrate was concentrated under reduced pressure. The residue was dissolved in chloroform (60 mL), and the solution was left to stand for one hour. Subsequently, the formed insoluble substance was removed through filtration, and the filtrate was concentrated under reduced pressure, to thereby yield 24.62 g of 3-amino-2,4-dichloro-6-methylpyridine (yield: 96%) as a colorless solid. The product was recrystallized from hexane, to thereby yield colorless crystals.

Example 39

Synthesis of N-(2,4-dichloro-6-methylpyridin-3-yl)-2-bromoacetamide

3-Amino-2,4-dichloro-6-methylpyridine (48.0 g, 271.1 mmol) was dissolved in chloroform (384 mL), and N,N-dimethylaniline (39.4 g, 325.1 mmol) was added to the solution. A solution of bromoacetyl bromide (65.7 g, 325.5 mmol) in chloroform (96 mL) was added dropwise to the mixture under stirring and under cooling with ice. The resultant mixture was stirred for 1 hour at the same temperature and for 1 hour at room temperature. Subsequently, under cooling with ice, a solution of bromoacetyl bromide (27.4 g, 135.7 mmol) in chloroform (48 mL) was further added to the resultant mixture, followed by stirring for 1 hour at room temperature. Water (288 mL) was added to the reaction mixture, and the resultant mixture was stirred for 12 hours at room temperature. The reaction mixture was stirred for 2 hours under cooling with ice, and the precipitated crystals were collected through filtration. The crystals were washed with cold ethanol (96 mL) and dried at 50° C. by use of a blower, to thereby yield 58.81 g of N-(2,4-dichloro-6-methylpyridin-3-yl)-2-bromoacetamide (yield: 73%) as colorless crystals.

The above filtrate and the wash liquid were combined together, and the organic layer was separated. The aqueous layer was extracted with chloroform (240 mL), and the resultant organic layer and the above-separated organic layer were combined together. The combined organic layer was washed with saturated brine (240 mL) and dried over sodium sulfate anhydrate, followed by condensation under reduced pressure. The residue was dissolved in chloroform (48 mL) at 60° C., and the solution was allowed to cool to room temperature, followed by stirring for 2 hours under cooling with ice. The precipitated crystals were collected through filtration, washed with cold chloroform (24 mL), and dried at 50° C. by use of a blower, to thereby further yield 12.83 g of N-(2,4-dichloro-6-methylpyridin-3-yl)-2-bromoacetamide (yield: 16%) as colorless crystals.

Example 40

Synthesis of N-(2,4-dichloro-6-methylpyridin-3-yl)-2-[4-(2-hydroxyethyl)-piperazin-1-yl]acetamide N-(2,4-Dichloro-6-methylpyridin-3-yl)-2-bromoacetamide (70.0 g, 234.9 mmol) was dissolved in acetonitrile (105 mL), and potassium carbonate (39.0 g, 282.2 mmol) was added to the solution under stirring and under cooling with ice. While the inner temperature was maintained at 5° C. or lower, a solution of 1-(2-hydroxyethyl)piperazine (36.7 g, 281.9 mmol) in acetonitrile(140 mL) was added dropwise to the resultant mixture. Thereafter, the temperature of the mixture was elevated to room temperature, and the mixture was stirred for 4 hours. The reaction mixture was extracted with chloroform-water, and the aqueous layer was further extracted twice with chloroform. The combined organic layer was washed with saturated brine and dried over sodium sulfate anhydrate, followed by condensation under reduced pressure. The residue was recrystallized from isopropanol and diisopropyl ether, to thereby yield 73.57 g of N-(2,4-dichloro-6-methylpyridin-3-yl)-2-[4-(2-hydroxyethyl)piperazin-1-yl] acetamide (yield: 90%) as colorless crystals.

Example 41

Synthesis of 2-[4-(2-hydroxyethyl)piperazin-1-yl]-N-[2,4-bis(methylthio)-6-methylpyridin-3-yl]acetamide N-(2,4-Dichloro-6-methylpyridin-3-yl)-2-[4-(2-hydroxyethyl)piperazin-1-yl]acetamide (58.0 g, 167.0 mmol) and 18-crown-6 (4.41 g, 16.7 mmol) were dissolved in dimethyl sulfoxide (580 mL), and sodium thiomethoxide powder (46.8 g, 667.7 mmol) was added to the solution under stirring and under cooling with ice, followed by stirring for 2.5 hours at an inner temperature of 65-75° C. The reaction mixture was allowed to cool to room temperature, and water was added to the mixture under cooling with ice, followed by extraction with chloroform. The aqueous layer was extracted with chloroform. The combined organic layer was washed with saturated brine and concentrated under reduced pressure. The residue was recrystallized from isopropanol and diisopropyl ether, to thereby yield 43.83 g of 2-[4-(2-hydroxyethyl)piperazin-1-yl]-N-[2,4-bis(methylthio)-6-methylpyridin-3-yl] acetamide (yield: 71%) as colorless crystals.

Example 42

Synthesis of 2-[4-(2-benzimidazol-2-ylthio)ethylpiperazin-1-yl]-N-[2,4-bis(methylthio)-6-methylpyridin-3-yl]acetamide 2-[4-(2-Hydroxyethyl)piperazin-1-yl]-N-[2,4-bis(methylthio)-6-methylpyridin-3-yl]acetamide (50.0 g, 134.9 mmol), 2-mercaptobenzimidazole (75.0 g, 499.3 mmol), and triphenylphosphine (125.0 g, 476.6 mmol) were dried under reduced pressure and dissolved in anhydrous N,N-dimethylformamide (500 mL). A solution of diethyl azodicarboxylate (DEAD) in toluene (DEAD: 40% w/v toluene solution, 168 mL, 385.9 mmol) was added dropwise to the resultant solution under stirring and under cooling with ice, and the mixture was stirred for 2 hours at the same temperature. Subsequently, the temperature of the mixture was elevated to room temperature, and the mixture was further stirred for 1 hour. The reaction mixture was partitioned by adding chloroform (500 mL) and 1 mol/L hydrochloric acid (500 mL), and the aqueous layer was collected and washed twice with chloroform (500 mL). Acetonitrile (250 mL) was added to the aqueous layer, and the aqueous layer was made basic by adding potassium carbonate, followed by stirring for 1 hour at room temperature. The precipitated crystals were collected through filtration, washed sequentially with water (300 mL) and acetonitrile (100 mL), and dried at 60° C. by use of a blower, to thereby yield 65.38 g of 2-[4-(2-benzimidazol-2-ylthio)ethylpiperazin-1-yl]-N-[2,4-bis(methylthio)-6-methylpyridin-3-yl]acetamide (yield: 96.4%) as slightly yellowish white crystals.

The invention claimed is:

1. A process for producing a hydroxyl alkyl cyclic diamine compound represented by the following formula (1):

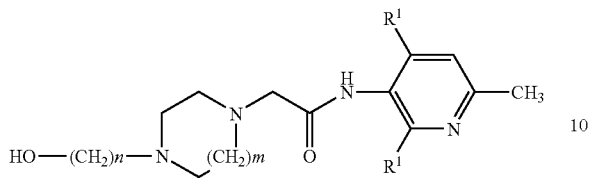

wherein
R$^1$ denotes a bromine atom,
m is 1 or 2, and
n is an integer of 1 to 6, which comprises:
reducing 2, 4-Dibromo-6-methyl-3-nitropyridine represented by the following formula (24)

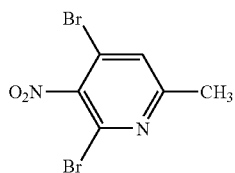

(24)

to 3-Amino-2, 4-dibromo-6-methylpyridine represented by the following formula (7a):

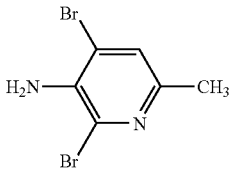

(7a)

and
acylating the 3-Amino-2,4-dibromo-6-methylpyridine to obtain an acetamide compound represented by the following formula (6):

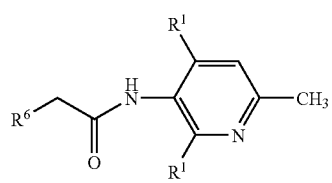

(6)

wherein
each of R$^1$ and R$^6$, which may be identical to or different from each other, is a halogen atom.

* * * * *